(12) United States Patent
Amano et al.

(10) Patent No.: US 8,475,828 B2
(45) Date of Patent: Jul. 2, 2013

(54) MEDICAL APPARATUS AND METHOD FOR PRODUCING SAME

(75) Inventors: Kenichi Amano, Shizuoka (JP); Yoshimi Akaike, Shizuoka (JP)

(73) Assignee: Covidien LP, Mansfield, MA (US)

( * ) Notice: Subject to any disclaimer, the term of this patent is extended or adjusted under 35 U.S.C. 154(b) by 82 days.

(21) Appl. No.: 13/238,459

(22) Filed: Sep. 21, 2011

(65) Prior Publication Data

US 2012/0009262 A1    Jan. 12, 2012

Related U.S. Application Data

(62) Division of application No. 11/906,195, filed on Oct. 1, 2007, now abandoned.

(30) Foreign Application Priority Data

Oct. 3, 2006 (JP) .................................. 2006-272020

(51) Int. Cl.
- *A61K 9/00* (2006.01)
- *A61K 31/7048* (2006.01)
- *A61K 31/7036* (2006.01)
- *A61P 31/00* (2006.01)

(52) U.S. Cl.
USPC ................ 424/423; 424/486; 514/40; 514/30

(58) Field of Classification Search
None
See application file for complete search history.

(56) References Cited

U.S. PATENT DOCUMENTS

| | | | |
|---|---|---|---|
| 4,642,104 A * | 2/1987 | Sakamoto et al. | ............ 604/264 |
| 4,917,686 A | 4/1990 | Bayston et al. | |
| 5,360,397 A | 11/1994 | Pinchuk | |
| 5,516,480 A | 5/1996 | Krall et al. | |
| 5,624,704 A * | 4/1997 | Darouiche et al. | ........... 427/2.24 |
| 5,902,283 A | 5/1999 | Darouiche et al. | |
| 6,214,370 B1 | 4/2001 | Nelson et al. | |
| 2005/0058835 A1* | 3/2005 | Howdle et al. | ............. 428/411.1 |
| 2005/0079199 A1 | 4/2005 | Heruth et al. | |
| 2005/0244459 A1 | 11/2005 | DeWitt et al. | |
| 2007/0026043 A1* | 2/2007 | Guan et al. | ..................... 424/426 |
| 2007/0281073 A1* | 12/2007 | Gale et al. | .................... 427/2.25 |

FOREIGN PATENT DOCUMENTS

| | | |
|---|---|---|
| JP | 03049768 A | 3/1991 |
| JP | 10211272 A | 8/1998 |
| JP | 10328294 A | 12/1998 |
| JP | 11-504241 | 4/1999 |
| JP | 11099200 A | 4/1999 |
| JP | 11299882 A | 11/1999 |
| JP | 2003070899 A | 3/2003 |
| JP | 2003070900 A | 3/2003 |
| WO | WO 96/33670 | 10/1996 |
| WO | WO 02/051464 | 7/2002 |

OTHER PUBLICATIONS

Rehab et al. "Nanocomposite materials based on polyurethane intercalated into montmorillonite clay". vol. 399, Issues 1-2, Jun. 15, 2005, pp. 368-376.*

Rehab et al. "Nanocomposite materials based on polyurethane intercalated into montmorillonite clay". vol. 399, Issue 1-2, Jun. 15, 2005, pp. 368-376.*

International Search Report from European Application No. EP 07 11 7729.9 dated Feb. 11, 2008.

* cited by examiner

*Primary Examiner* — Robert A Wax
*Assistant Examiner* — Danah Al-Awadi

(57) ABSTRACT

A medical device that includes at least one antibiotic in a macromolecular substance that swells upon contact with a solvent. Also, a method for preparing an antibiotic-containing medical device that involves contacting a medical device having at least a portion of the surface formed from a swellable macromolecular substance, with a solvent that swells the macromolecular substance, contacting the swollen macromolecular substance with at least one antibiotic, and removing the solvent from the swollen macromolecular substance.

8 Claims, No Drawings

MEDICAL APPARATUS AND METHOD FOR PRODUCING SAME

CROSS-REFERENCE TO RELATED APPLICATIONS

This application is a divisional application of U.S. patent application Ser. No. 11/906,195, filed on Oct. 1, 2007 which, in turn, claims the benefit of and priority to Japanese Patent Application No. 2006-272020 filed on Oct. 3, 2006, the entire disclosures of each of which are hereby incorporated by reference herein.

TECHNICAL FIELD

The present disclosure is related to a production method for a medical apparatus, a method for applying antibiotics to the surface of a medical apparatus, and the medical apparatus to which antibiotics are applied.

BACKGROUND

An intravascular catheter is used for providing central venous nutrition and performing dialysis treatment. It may be desirable for medical devices that have a portion thereof placed inside the body to have an antimicrobial layer formed thereon. Antimicrobial layers may be formed with an antimicrobial agent such as antibiotics coated on the surface. In embodiments, the antimicrobial agent may be continually released from the surface while inside the body.

Therefore, there are proposals for various technologies for coating the surface of a medical apparatus with an antimicrobial agent. For example, JP Patent H11-504241 produces an antimicrobial composition by dissolving an antimicrobial agent in an organic solvent and adding an alkalising agent. This composition may be used to form a coating on the surface of a catheter and the like. However, as most antibiotics that include antimicrobial agents have high polarity and do not dissolve in an organic solvent, the above method is only feasible with only a few antibiotics having low polarity, and can not be applied to most antibiotics.

SUMMARY

The present disclosure includes methods of manufacturing medical devices, including manufacturing medical devices with the application of most antibiotics on the surface regardless of whether polarity is high or low, as well as methods of applying antibiotics on the surface of medical devices regardless of the polarity of the antibiotic, and medical devices on which antibiotics have been applied.

As noted above, the present disclosure provides methods for manufacturing medical devices and/or medical equipment with at least a portion of the surface having antibiotics applied thereto. In embodiments, the methods include forming a swollen area on at least a portion of the surface of the medical device by causing a medical device formed using a macromolecular material that can swell to come into contact with a solvent, causing the swollen area to come into contact with antibiotics, and removing the solvent from the swollen area that has come into contact with the antibiotics.

In addition, the present disclosure provides methods for applying antibiotics to the surface of medical devices. This method may include forming a swollen area on a portion of the surface of the medical device by causing the medical device, formed using a macromolecular material that can swell, to come into contact with a solvent, causing the swollen area to come into contact with antibiotics, and removing the solvent from the swollen area that came into contact with the antibiotics.

In embodiments, a method of the present disclosure for preparing an antibiotic-containing medical device may include providing a medical device having at least a portion of the surface formed from a swellable macromolecular substance, contacting the medical device with a solvent that swells the macromolecular substance, contacting the swollen macromolecular substance with at least one antibiotic, and removing the solvent from the swollen macromolecular substrate.

In addition, the present disclosure provides medical devices with antibiotics applied to at least a portion of their surface. The medical device surface may be contacted with a solvent so that at least a portion of the surface forms a swollen area, and the swollen area is caused to contact the antibiotics, and afterwards, the solvent is removed from the swollen area.

In embodiments, a medical device of the present disclosure may include a synthetic resin including a macromolecular substance that swells upon contact with a solvent, and at least one antibiotic in the macromolecular substance.

In embodiments, the antibiotic may be a water soluble antibiotic and the solvent may be an aprotic polar solvent. Examples of water soluble antibiotics include, but are not limited to, isepamicin sulphate, amikacin sulphate, tobramycin, kitasamycin tartrate, and combinations thereof. Furthermore, aprotic polar solvents may include, but are not limited to, dimethylformamide, dimethyl sulphoxide, dimethylacetamide, and combinations thereof.

By causing medical devices to come into contact with a solvent, the solvent may penetrate into the contact area of the medical device and the aforementioned contact area of the medical device swells. Afterwards, by causing the swollen area to come into contact with antibiotics, the antibiotics may enter into the swollen area.

In embodiments, the swollen area of the medical device may be formed from a macromolecular material such as a synthetic resin that can swell due to the solvent; in embodiments, the intervals between macromolecules of the synthetic resin expand upon exposure to the solvent. Furthermore, if the swollen area is formed using a macromolecular material that has cross-linking, the three dimensional meshwork formed by the macromolecules may be expanded due to the swelling that occurs upon application of the solvent. Therefore, antibiotics may enter in between the macromolecules that have been expanded in this manner.

Afterwards, the solvent may be removed from the swollen area and the area that had swollen thus shrinks and returns to its previous state. This shrinkage causes the antibiotics that entered in between the macromolecules that form the area that was swollen to be captured in this area. The captured antibiotics may bond structurally and physically with the medical device and provide a sustained release from the surface of the medical device when the medical device is actually used, functioning as an antimicrobial agent.

Thus, in accordance with the present disclosure, the intervals between the macromolecules that form the swollen area of medical devices may be expanded through swelling, antibiotics may enter in between the expanded macromolecules, and afterwards the swelling may be reversed, capturing the antibiotics that entered in between the expanded macromolecule, thereby bonding the antibiotics structurally and physically in the medical device. Therefore, the methods of the present disclosure differ from the conventional method of bonding the antibiotic to medical devices using chemical bonding, thereby enabling the application of antibiotics to the surface of the medical device regardless of polarity of the antibiotic.

In accordance with the present disclosure, at least a portion of the surface of the medical device may include a meshwork structure where the macromolecules form a meshwork structure through entanglement, cross-links of the macromolecular chain, or both. Antibiotics may be retained in this meshwork structure and thus may be structurally and/or physically captured in the medical device.

DETAILED DESCRIPTION

The present disclosure provides methods for manufacturing medical devices and methods for applying antibiotics to at least a portion of the surface of the medical device. Medical devices that may be produced in accordance with the present disclosure include those that may be introduced into the body transdermally or transluminally and remain in the body for a prescribed period usually require application of antibiotics on the surface to prevent bacterial infection. Specific examples of these types of medical devices include catheters and tubes.

The methods of the present disclosure may include a swelling step, an antibiotics contacting step, and a solvent removal step. In the swelling step, a medical device that is formed with a macromolecular material that can swell, is caused to come into contact with a solvent thereby forming a swollen area on at least a portion of the surface of the medical device. The medical device used in this step is not restricted to those requiring application of antibiotics to the surface thereof.

The material utilized to form the medical device can be any material where at least a portion of the surface swells through contact with a solvent. The solvent may penetrate inside the macromolecules forming the medical device and form a swollen area in the medical device. If at least a portion of the surface of the medical device is formed out of a material that can swell, the other areas can be formed out of a material that does not swell. Of course, the entire device can be formed out of a material that can swell and partial swelling can be obtained by causing only the portion that needs to swell to come into contact with the solvent. In embodiments, a macromolecular material that can be swollen using a solvent, where antibiotics are to be applied, may be made of synthetic resin. In embodiments, at least a portion of the surface of the medical device may be the swollen portion, or the entire surface can become the swollen portion, i.e., the entire medical device can be caused to swell.

The material utilized to form the medical device may be selected based on lubrication and elastic characteristic. In embodiments, medical devices may be formed of synthetic resins, including polyurethane synthetic resins, polyamide synthetic resins, combinations thereof, and the like. These types of materials include macromolecular compounds and can swell depending on the solvent. In order to more effectively produce swelling, a solvent with an SP (Solubility Parameter) that is close to these materials can be selected.

Furthermore, in the swelling process, the medical device may be contacted with the solvent by immersion, coating, combinations thereof, or the like. Immersion may be desirable for effective swelling of the medical device. Furthermore, if shaking is performed during immersion, swelling can occur more quickly.

In accordance with the present disclosure, an antibiotic contact step may be performed after the swelling step. In this antibiotic contact step, the swollen area from the swelling step is contacted with antibiotics. There are no restrictions on the method of causing this contact, but immersion of the aforementioned swollen area in a solution that contains the antibiotic may be desirable in some embodiments. As noted above, the space between macromolecules in the structure of the swollen area is expanded by the solvent in the swell step. By causing contact with antibiotics in this state, the antibiotics may enter in between the macromolecules that are the structure for the swollen area. The antibiotics thus penetrate into the swollen area. Here, in the case that the macromolecular compound that makes up the structure for the swollen area is cross-linked, the antibiotic may be mixed into the three dimensional meshwork structure formed by this cross-linking.

As noted above, the solvent in the swelling step expands the interval between the macromolecules that form the structure of the swollen area. Because the solvent molecules enter between the macromolecules in the swollen area, unless the affinity of the solvent and antibiotic is high, the molecules that make up the structure of the antibiotic may be blocked by the solvent molecules and the antibiotic may not be able to enter into the spaces between the macromolecules. Therefore, antibiotics and solvents that have high affinity may be selected so that this does not occur.

For example, where water soluble isepamicin sulphate is used as the antibiotic, as isepamicin sulphate has a high polarity and is water soluble, a solvent that also has a high polarity may be selected. Furthermore, as isepamicin sulphate has a plurality of hydroxyl groups, if the solvent also has hydroxyl groups, there is the possibility that that the two sets of hydroxyl groups will generate a dehydration reaction. Therefore, an aprotic solvent may be selected to prevent this type of reaction. As has been described, in the case that a water soluble antibiotic is used, use of an aprotic polar solvent as the solvent may be desirable. In other words, if an aprotic polar solvent is used as the solvent, soluble antibiotics can be applied to the surface of medical devices.

Examples of suitable water soluble antibiotics include isepamicin sulphate, amikacin sulphate, tobramycin, kitasamycin tartrate, combinations thereof, and the like. Examples of aprotic polar solvents which may be utilized include dimethylformamide (DMF), dimethyl sulphoxide (DMSO), dimethylacetamide (DMAC), 2-butanone, acetone, acetinitrile, N-methylpyrrolidone, combinations thereof, and the like. Of these, DMF, DMSO, and DMAC have a slow evaporation speed compared to the other solvents, so that when the antibiotic contacts the swollen area in the antibiotic contact step, it is less likely that the solvent that has contacted the swollen area will be prematurely evaporated or the swelling will be prematurely reversed. Therefore, these solvents may be advantageous in some embodiments.

Furthermore, a solvent removal step may be performed after the antibiotic contact step. In this solvent removal step, the solvent may be removed from the swollen area. The swelling is reversed through removal of the solvent and the swollen area shrinks to return to its previous state. This shrinking narrows the space between macromolecules in the swollen area, and in the end the antibiotic is captured, i.e. retained, in the swollen area. Therefore, the antibiotic structurally and physically bonds with the swollen area of the medical device. This bond is a physical bond and, as it is not a chemical bond, the antibiotic bonds with the medical device regardless of polarity. Any suitable method can be used for the solvent removal method. In embodiments, solvent removal can be performed by drying, washing, combinations thereof, and the like.

The following Examples are being submitted to illustrate embodiments of the present disclosure. The Examples are intended to be illustrative only and are not intended to limit the scope of the present disclosure.

EXAMPLE 1

Manufacture of a catheter tube to which antibiotics are applied. A catheter tube made of polyurethane with a diameter of 14 G (outer diameter approximately 2.1 mm) and a total length of about 20 cm was obtained. Next, this catheter tube was immersed in dimethylformamide as the solvent for about 30 minutes with agitation (swell step). A swollen area was formed on the surface of the catheter tube as a result of this agitated immersion.

After performing agitated immersion for about 30 minutes, the catheter tube was lifted out of the dimethylformamide. Next, the catheter tube was immersed in a water solution containing about 100 mg/ml isepamicin sulphate as an antibiotic and was agitated for about 30 seconds at room temperature (antibiotic contact step). This agitated immersion caused the isepamicin sulphate to be captured in the swollen area of the surface of the catheter tube.

After performing agitated immersion for about 30 seconds, the catheter tube was lifted out of the aforementioned water solution. Next, the catheter tube was dried for about 3 hours at about 50° C. thereby removing the dimethylformamide from the swollen area (solvent removal step). A catheter tube with isepamicin sulphate applied to the surface was thus manufactured through the aforementioned steps.

EXAMPLE 2

Manufacture of a Sample. The catheter tube manufactured above in Example 1 was cut to a length of about 1 cm and used as test piece 1. Furthermore, as a comparative example product, the above swelling step was omitted and a catheter tube was manufactured using only the above antibiotic contact step and above solvent removal step. This comparative tube was cut to about 1 cm and used as test piece 2. Furthermore, commercially available catheter tubes A, B, and C, having antimicrobial properties, were prepared by cutting to the same length as aforementioned test piece 1 and designated as test pieces 3, 4, and 5, respectively. The commercially available products A, B, C are described below:

Commercially available product A—product name ARROWgard® Blue manufactured by Arrow International;

Commercially available product B—product name COOK SPECTRUM® manufactured by COOK CRITICAL CARE; and Commercially available produce C—product name Edwards Vantex manufactured by Edwards Lifescience.

The antimicrobial agents applied to commercially available product A are chlorhexidine and sulphadiazine silver; the antibiotics applied to commercially available product B are minocycline hydrochloride and rifampicin; and the antimicrobial agent applied to commercially available product C is silver.

EXAMPLE 3

Antimicrobial test (inhibition circle test). First, the following bacteria were prepared as bacterium for testing:
Bacteria 1: *Staphylococcus aureus*;
Bacteria 2: *Pseudomonaus aeruginosa*; and
Bacteria 3: *Escherichia coli*.

Each bacteria was cultured for about 24 hours at about 37° C. on an SCD (soybean, casein, digest) agar plate. Afterwards, each of the cultured bacteria were suspended in approximately $10^7$ CFU/ml equivalent using normal saline solution (that had been sterilised) and a suspension of bacteria (bacteria suspension) was prepared.

Next, the SCD agar plate (as the culture medium for forming an inhibition circle) was steam sterilised in an Erlenmyer flask and afterwards cooled to about 50° C. in a bath. After cooling, about 1/10 of the volume of each bacteria suspension was placed on separate SCD agar plates, and agar plates containing bacteria strains (agar plate containing indicator-strains) were prepared for each bacteria.

Agar plates containing indicator-strains were put in 8 cm diameter sterilised Petri dishes and the agar plate was solidified inside this Petri dish. After solidification, a hole roughly the size of the outer diameter of the test pieces was formed in the center of the agar plates and the test pieces were inserted in these holes. In addition, the agar dishes containing the indicator-strains were placed on top and this was solidified.

In the manner described above, agar dishes with indicator strains for each type of test piece 1 to 5 were prepared for all three types of bacteria (thus a total of 15) and these were cultured for about 24 hours at a temperature of about 37° C. After culturing, the diameter of the inhibition circle formed by the antimicrobial agent was measured. The measurement results are shown in Table 1.

TABLE 1

Measurement Results (diameter of zone of inhibition) (Unit: mm)

| Sample | Organism | | |
|---|---|---|---|
| | S. aureus | P. aeruginosa | E. coli |
| Test piece 1 (Example 1) | 46 | 16 | 20 |
| Test piece 2 (Comparative tube) | 0 | 0 | 0 |
| Test piece 3 (Commercial Product A) | 29 | 20 | 23 |
| Test piece 4 (Commercial Product B) | 40 | 12 | 15 |
| Test piece 5 (Commercial Product C) | 22 | 6 | 6 |

As can be seen from Table 1, test piece 1, created in accordance with the present disclosure, formed an inhibition ring for each of the bacteria, showing sufficient antimicrobial effect similar to commercially available product A (test piece 3), commercially available product B (test piece 4), and commercially available product C (test piece 5). On the other hand, the comparison example (test piece 2) did not form an inhibition ring for any of the bacteria and did not exhibit any antimicrobial effect.

From the above results, the catheter tube created in accordance with the present disclosure (test piece 1) clearly had antibiotic reliably applied to the surface of the tube and exhibited antimicrobial effects. Furthermore, as can be seen from the aforementioned results of test piece 2, unless the catheter tube was caused to swell, the antibiotics did not adhere to the surface of the catheter tube. It follows, with investigation of these results as well, that antibiotics penetrated the surface of the tube through swelling of the catheter tube for test piece 1 and, by reversing the swelling, the antibiotics were captured on the surface of the tube. The captured antibiotics were thus under a controlled release profile and an antimicrobial effect was exhibited.

It will be appreciated that various of the above-disclosed and other features and functions, or alternatives thereof, may be desirably combined into many other different systems or applications. Also that various presently unforeseen or unanticipated alternatives, modifications, variations or improvements therein may be subsequently may by those skilled in the art which are also intended to be encompassed by the following claims. Unless specifically recited in a claim, steps or components of claims should not be implied or imported from the specification or any other claims as to any particular order, number, position, size, shape, angle, color, or material.

What is claimed is:

1. A method for preparing an antibiotic-containing medical device comprising:
providing a medical device having at least a portion of the surface formed from a swellable macromolecular substance; swelling said macromolecular substance by contacting it with an aprotic polar solvent; then contacting the swollen macromolecular substance with at least one water-soluble antibiotic dissolved in an aqueous solution; and removing residual solvent.

2. The method of claim 1 wherein the medical device comprises a synthetic resin.

3. The method of claim 2 wherein the synthetic resin is selected from the group consisting of a polyurethane, a polyamide, and combinations thereof.

4. The method of claim 1 wherein the aprotic polar solvent is selected from the group consisting of dimethylformamide, dimethyl sulphoxide, dimethylacetamide, 2-butanone, acetone, acetonitrile, N-methylpyrrolidone, and combinations thereof.

5. The method of claim 1 wherein the water soluble antibiotic is selected from the group consisting of isepamicin sulphate, amikacin sulphate, tobramycin, kitasamycin tartrate, and combinations thereof.

6. The method of claim 1, wherein the antibiotic is retained within the macromolecular substance.

7. The method of claim 1, wherein at least a portion of the macromolecular substance comprises a meshwork structure, and the antibiotic is retained in said meshwork structure.

8. The method of claim 1 wherein the solvent is removed from the swollen macromolecular substance by a method selected from the group consisting of drying, washing, and combinations thereof.

* * * * *